(12) United States Patent
Weitzel et al.

(10) Patent No.: US 10,350,035 B2
(45) Date of Patent: Jul. 16, 2019

(54) PLACEMENT DEVICE FOR A DENTAL COMPONENT

(71) Applicant: NOBEL BIOCARE SERVICES AG, Kloten (CH)

(72) Inventors: Jörg Weitzel, Rielasingen-Worblingen (DE); Roberto Carretta, Zug (CH)

(73) Assignee: Nobel Biocare Services AG, Kloten (CH)

( * ) Notice: Subject to any disclaimer, the term of this patent is extended or adjusted under 35 U.S.C. 154(b) by 0 days.

(21) Appl. No.: 15/737,716

(22) PCT Filed: Jun. 16, 2016

(86) PCT No.: PCT/EP2016/063831
§ 371 (c)(1),
(2) Date: Dec. 18, 2017

(87) PCT Pub. No.: WO2016/202900
PCT Pub. Date: Dec. 22, 2016

(65) Prior Publication Data
US 2018/0193115 A1    Jul. 12, 2018

(30) Foreign Application Priority Data

Jun. 19, 2015   (EP) .................... 15172906

(51) Int. Cl.
*A61C 8/00*        (2006.01)
*A61C 13/225*      (2006.01)
(52) U.S. Cl.
CPC .......... *A61C 8/0089* (2013.01); *A61C 13/225* (2013.01)
(58) Field of Classification Search
CPC ................ A61C 8/0089; A61C 13/225
See application file for complete search history.

(56) References Cited

U.S. PATENT DOCUMENTS 5,626,474 A * 5/1997 Kukla ............. A61C 8/0089
                                        433/141
7,100,476 B1 * 9/2006 Feit .................. A61B 17/8875
                                        433/114
(Continued)

FOREIGN PATENT DOCUMENTS

EP      1267744 B1    4/2009
EP      2127612 A1   12/2009
(Continued)

OTHER PUBLICATIONS

International Search Report for Application No. PCT/EP2016/063831 dated Sep. 16, 2016 in 4 pages [the ISR for the PCT Application of this US national phase application].

*Primary Examiner* — Ralph A Lewis
(74) *Attorney, Agent, or Firm* — Knobbe Martens Olson & Bear LLP (57) ABSTRACT

The present invention relates to a placement device for a dental component, a method for handling a dental component with a placement device, a dental component for placement with a placement device and a set comprising a placement device and a dental component. The placement device (1) for a dental component (2) is preferably an implant and comprises a proximal end (11), a distal end (12) and a coupling mechanism (20) for coupling the distal end (12) to the dental component. The coupling mechanism includes at least one movable pin (21) having a longitudinal axis (A1) and being movable along its longitudinal axis (A1) relative to the placement device (1) for engaging the dental component. It also includes at least one engagement part (28) at the distal end of the placement device (1) for engaging the dental component, the engagement part having a longitudinal axis (A2). A secure interlock between the dental component and the placement device is achieved by (Continued)

arranging the longitudinal axis (A2) of the engagement part (28) at an angle (α) relative to the longitudinal axis (A1) of the movable pin (21).

15 Claims, 3 Drawing Sheets

(56) References Cited

U.S. PATENT DOCUMENTS

| | | | | |
|---|---|---|---|---|
| 2003/0162149 A1* | 8/2003 | Bjorn | ............... | A61C 8/005 |
| | | | | 433/173 |
| 2009/0298013 A1* | 12/2009 | Baruc | ............... | A61C 8/005 |
| | | | | 433/174 |
| 2011/0287386 A1* | 11/2011 | Better | ............... | A61C 8/0018 |
| | | | | 433/174 |
| 2015/0342708 A1* | 12/2015 | Haus | ............... | A61C 8/0068 |
| | | | | 433/201.1 |

FOREIGN PATENT DOCUMENTS

| | | |
|---|---|---|
| WO | WO 2010/146573 A1 | 12/2010 |
| WO | WO 2014/095033 A1 | 6/2014 |
| WO | WO 2016/009320 A2 | 1/2016 |

\* cited by examiner

PLACEMENT DEVICE FOR A DENTAL COMPONENT

CROSS-REFERENCE TO RELATED APPLICATIONS

This application is a national stage application under 35 U.S.C. § 371 of International Application No. PCT/EP2016/063831, filed on Jun. 16, 2016, which published in English as WO 2016/202900 A1 on Dec. 22, 2016, and which claims priority benefit of EP Patent Application No. 15172906.8, filed on Jun. 19, 2015.

TECHNICAL FIELD

The present invention relates to a placement device for a dental component, a method for handling a dental component with a placement device, a dental component for placement with a placement device and a set comprising a placement device and a dental component.

PRIOR ART

Dental components used in the art of dentistry are relatively small and prone to the risk of getting lost if not reliably secured during a procedure. Once lost, a swallowing reflex of the patient may cause such a component to enter the patient's throat. There is also the risk that the dental component gets introduced into a patient's airway as a result of a breathing reflex. These potentially detrimental events are most likely to occur during placement or removal of a dental component within the oral cavity of a patient.

Further, a dental component may also fall down during handling outside the oral cavity, for example during transfer of the component to a patient after having been removed from its packaging. If hitting another object, these components may get damaged. Metallic dental components are likely to be deformed, whereas brittle materials such as ceramics may more likely experience chipping. Replacement of such a damaged component in dentistry is often hard to come by, particularly if the dental component is customized. Further, losing control over the component can result in an increased exposure to a potentially detrimental environment, making resterilization necessary. As a result, the chair time of a patient is prolonged, which is not only inconvenient for the patient but also generates additional costs.

In order to avoid such problems, devices for handling dental components have been proposed such as the hand tool for dental prosthetics disclosed in US 2006/0131906 A1. The hand tool comprises a grip part, which has in the front end area an open receiving recess with a collet element arranged in the receiving recess for receiving an object. The tool further includes an actuating device for the collet element.

However, a collet element is merely gripping the dental component from the side and clamps said component to the hand tool. In order to enable the application of torque with such a hand tool, the collet element requires a hard grip, which bears the risk of straining the dental component, or requires structural features on the gripping surface, which allow for a transmission of torque from the collet element to a dental component. With the latter approach, the structural features tend to transform a part of the torque applied with the hand tool into a force directed outwards in relation to the collet element. Since this force urges the collet element to open up, additional features such as a locking mechanism are required to prevent the loosening of the grip and, thus, the loss of the dental component. As a result, the hand tool is more bulky at its connecting interface and is rendered more complex.

Having in mind these observations, it was an objective of the present invention to provide a placement device for a dental component that provides a reliable and secure connection. Still, the connection between the placement device and the dental component should be easily releasable once the dental component is placed at its predetermined position. In other words, it was an object of the invention to find a solution for the concurrent aims of establishing a tight connection and ensuring a facile release. Moreover, the application of torque should not interfere with the coupling mechanism between the placement device and the dental component.

It was another objective of the present invention to reduce any risks that may result from environmental exposure of the dental component. Also, the placement device should have a more compact design so that it can be easily navigated in small spaces within the oral cavity without interfering with adjacent teeth, gum tissue or bone tissue.

SUMMARY OF THE INVENTION

Aforementioned objectives have been addressed with the present invention and its solution is defined in the independent claims, wherein the dependent claims specify further embodiments of the invention.

More specifically, the present invention provides a placement device for a dental component, which is preferably an implant. The placement device comprises a proximal end, a distal end and a coupling mechanism for coupling the distal end to the dental component. The coupling mechanism includes at least one movable pin having a longitudinal axis and being movable along its longitudinal axis relative to the placement device for engaging the dental component. Said mechanism also includes at least one engagement part at the distal end of the placement device for engagement with the dental component, the engagement part also having a longitudinal axis, wherein the longitudinal axis of the engagement part is arranged at an angle relative to the longitudinal axis of the movable pin.

The placement device according to the present invention having the features as defined above offers a secure attachment of a dental component in all six degrees of freedom. Thus, the coupling between the placement device and the dental component allows a user to apply force as well as torque without the risk of unintended release of the dental component. This renders the placement device applicable for a wide variety of dental procedures.

Owing to the engagement part and the movable pin being oriented at an angle other than zero to each other, a firm and reliable connection is achieved once these two features are in engagement with a dental component. This engagement is achieved by a form fit or positive locking fit. This form fit is not affected by the application of torque, i.e. there is no significant effect on the form fit such as loosening or fastening the connection, particularly if the form fit is established in a plane on which the rotational axis of the torque is situated. As a result, the placement device according to the invention also ensures an easy release of the dental component.

The structure of the placement device as defined above enables a secure connection to a dental component without the dental component requiring any additional features on its circumference due to the placement of the features establishing the engagement. As a result, both the dental component and the placement device can be designed more compact than the handling devices of the prior art so that interference with adjacent teeth, gum tissue or bone tissue during a procedure is significantly reduced.

The engagement part may be a pin, preferably a fixed pin, and/or a recess. Preferably the geometry of the engagement part is chosen to correspond to existing structures of the dental component such as features intended for the attachment of other dental components. For example, the dental component may be a dental implant such as a zygomatic implant to which other dental components such as spacers, abutments, multiunit abutments, superstructures or prostheses can be mounted.

It is to be understood in the context of the present invention that the longitudinal axis is the line extending in the direction of the length of the movable pin and/or recess, i.e. the longitudinal axis is running lengthwise of the movable pin and/or recess. For instance, if the movable pin is formed as a curved movable pin, the longitudinal axis of the pin is likewise curved; the part of the pin engaging the implant is then arranged at an angle relative to the longitudinal axis of the engagement part.

More than one engagement part and/or movable pin may be used to increase the strength of the connection between the placement device and the dental component.

For establishing a connection to a dental component, the movable pin is movable between a retracted and an extended position. In the retracted position, the engagement part is brought into engagement with the dental component so that a guide hole within the dental component is in alignment with the trajectory of the movable pin. Once in engagement, the movable pin can be introduced into said guide hole, thereby establishing the aforementioned form fit.

In a preferred embodiment of the placement device, the engagement part is aligned along a longitudinal axis of the placement device.

The orientation of the engagement part in this embodiment has the advantage that the connection between the placement device and the dental component can simply be established by moving the device straight towards the component without any movements sideways that may cause an interference with neighbouring objects.

More specifically, the longitudinal axis of the placement device in this embodiment basically coincides with the direction of motion while the placement device approaches the dental component for coupling. In other words, the engagement direction of the engagement part is chosen so that engagement is achieved directly without any movements sideways. In a second step, the movable pin is then moved to its extended or deployed position into engagement with the dental component at an angle in relation to the longitudinal axis of the engagement part.

Since the longitudinal axis of the movable pin is arranged at an angle in relation to the longitudinal axis of the engagement part, the movable pin may be flexible so that it can be redirected within the distal end of the placement device before entering the dental component. In this way, the design of the placement device can be more compact at its distal end, providing more space for navigation within the oral cavity of a patient.

In a further preferred embodiment, the longitudinal axis of the engagement part is arranged at an angle other than zero relative to the longitudinal axis of the movable pin. In particular, the movable pin is aligned along a longitudinal axis of the placement device.

In this embodiment, an actuation means for the movable pin is formed such that the movable pin can be retracted and extended along the longitudinal axis of the placement device, i.e. no redirection of the movable pin is necessary. This allows for a simple and reliable design of the actuation means for the movable pin, in particular when combined with an engagement part formed as a fixed pin or fixed recess.

In another preferred embodiment, the coupling mechanism of the placement device further comprises an actuation means for moving said movable pin between a retracted position and an engaged position.

The actuation means enables a user to set the movable pin manually into motion. Thus, the actuation means facilitates the engagement and/or disengagement of the dental component with the placement device. In other words, a user is able to at least initiate the engagement or disengagement with a dental component. The placement device is preferably designed to facilitate this action with one hand, which allows an even easier handling of the dental component while navigating in the oral cavity of a patient.

In another embodiment, the aforementioned actuation means is adapted to apply a rotation to the movable pin.

The rotation of the movable pin during its movement in at least one direction between the retracted and engaged position causes the engagement and/or disengagement. In other words, the movable pin may act like a hook. Naturally, the orientation of the longitudinal axis of the pin at the interface between the placement device and the dental component still has to differ from the orientation of the longitudinal axis of the engagement at said interface.

If a rotation is applied in the longitudinal direction of the movable pin on top of a translation, the movement of the pin in the guide hole of the dental component is smoother during engagement and disengagement. Further, the rotation may also be part of a mechanism of the aforementioned actuation means, such as a screw mechanism for converting a rotational movement into a translational movement or vice versa.

In another particularly preferred embodiment of the present invention, the actuation means comprises a drive mechanism for at least assisting in the extension and/or retraction of said movable pin.

Incorporating a drive mechanism into the placement device makes the handling of the device particularly easy for a user. The user only has to initiate the movement of the movable pin in at least one direction, whereas the work necessary for the actual movement of the pin is performed or provided by the drive mechanism. Thus, the placement device of this embodiment is not only usable with one hand but also only requires minimal movement of the hand or a finger. As a result, it is even easier to place a dental component with high precision and decrease the risk of misplacement during retraction or extension of the movable pin due to operating the coupling mechanism of the placement device.

The drive mechanism according to the invention at least assists in moving the movable pin in one direction. In this case, it is preferred that the movement of the movable pin in the other direction is used for biasing the drive mechanism. The biased drive mechanism may act similar to a ball pen mechanism and stores the energy necessary to retract or extend the movable pin. Mechanical means that may be used to design such a mechanism include springs, sliders, wedges, keys, threads and cams. Preferably, the drive mechanism does not only assist in moving the movable pin but performs said movement during extension and/or retraction on its own.

In a preferred embodiment of the placement device, the angle between the longitudinal axis of the movable pin and the longitudinal axis of the engagement part is between 3° to 80°, preferably between 20° and 60° and more preferably between 25° to 50°.

These angles have shown to establish a secure connection between the placement device and a dental component. The quality of the connection has a tendency to improve according to the ranges listed above. It has been found that a higher angle allows for a better force transmission. Lower angles, on the other hand, require less space in the width direction, i.e. sideways, of the placement device and the dental component.

In yet another embodiment, the placement device comprises a locking mechanism arranged to lock the position of the movable pin in its retracted and/or engaged position.

The locking mechanism has the advantage that it is not possible to accidentally move the movable pin before the engagement between the engagement part and a dental component is established. Such an unintended premature movement of the movable pin is particularly challenging for a user such as a dentist, when navigating the dental component within the oral cavity of a patient. The locking mechanism also prevents any damage that may be caused by the premature movement of the movable pin.

More specifically, the locking mechanism locks the movable pin in its retracted position until the engagement part is properly engaged with a dental component. Only if this condition is fulfilled, the locking mechanism releases the movable pin so that the engagement between the placement device and the dental component takes place in a predetermined relative position to each other.

The invention further provides a dental component for coupling to a placement device, in particular a placement device as described above. The dental component comprises a proximal end and a distal end, wherein the proximal end constitutes an interface for engagement with the placement device. The interface comprises at least one first engagement section having a first longitudinal axis defined therethrough and at least one second engagement section having a second longitudinal axis defined therethrough, wherein the first longitudinal axis is arranged at an angle relative to the second longitudinal axis.

A dental component having these features facilitates a secure connection or engagement with a placement device for handling and transmitting force and torque while minimizing the risk of unintended disengagement of the dental component.

Used with a placement device as previously described, the first engagement section interacts with the at least one movable pin and the second engagement section interacts with the at least one engagement part. Thus, the first engagement section is preferably formed as a recess such as a guide hole for receiving said movable pin. The second engagement section may be constituted by a recess and/or a protrusion in order to correspond to the engagement part of the placement device.

As already described, the dental component may be an implant, such as a dental or zygomatic implant, an abutment, a multiunit abutment, a superstructure such as a bridge, a prosthetic tooth or prosthetic teeth, dentures and the like.

In another embodiment of the dental component, the first engagement section of the dental component is arranged within the second engagement section.

This arrangement of the first engagement section and the second engagement section minimizes the area of the dental component exposed to the environment, particularly the oral flora of a patient after placement of the dental component within the oral cavity. More specifically, the first engagement section can be sealed off e.g. by placing another dental component on the dental component, since the first engagement section is arranged within the second engagement section.

Preferably, the second engagement section constitutes a part of the dental component that is intended for a connection with another dental component. For example, the second engagement section may be intended for mounting another dental component such as an abutment. This abutment then seals the first engagement section so that contact of the first engagement section with the oral flora of a patient is successfully prevented.

The present invention further provides an implantation set comprising a placement device as described above and a dental component according to one of the previously described embodiments, in particular an implant.

The implantation set according to the present invention has the advantage that it may be preassembled before the treatment of a patient begins. Preferably, the assembly takes place at the place of origin of the dental component, for example a production facility or a dental laboratory, so that it can be provided sterilized and ready for insertion at a dentist's office. If the placement device comprises a drive mechanism, the drive mechanism may already be biased in order to facilitate the actuation of the movable pin.

The present invention also provides a method for handling a dental component with a placement device, in particular the aforedescribed placement device, the method comprising the following steps. In one step, the placement device is moved along or about a first axis for engaging at least one engagement part situated at a distal end of the placement device with a second engagement section of the dental component. In another step of the method, at least one movable pin of the placement device is inserted into a first engagement section of the dental component along or about a second axis. The engagement part and the movable have a longitudinal axis, respectively, wherein the orientation of the longitudinal axis of the engagement part differs from the orientation of the longitudinal axis of the movable pin.

The interaction of the placement device and a dental component creates a reliable interlock between these two components. The interlock is established by advancing the movable pin after engagement between the engagement part of the placement device and the corresponding engagement section of the dental component. The insertion of the movable pin into the dental component establishes an interlock between the dental component and the placement device in all six degrees of freedom providing all the advantages already referred to in the description from above.

If the movable pin and/or the engagement part are brought into engagement about an axis, i.e. by a rotational movement, the orientations of the longitudinal axis at the interface between the placement device and the dental component still have to differ in order to achieve the form fit described above, which in turn provides the secure interlock.

In a preferred embodiment of the method, the engagement of the engagement part releases a locking mechanism of the placement device for enabling a movement of the movable pin.

This embodiment ensures a proper alignment between the interface of the placement device and the interface of the dental components before any actuation of the movable pin.

Thus, this embodiment additionally prevents any damage to the movable pin and said interfaces.

In another preferred embodiment of the present invention's method, the insertion and/or retraction of the movable pin is at least assisted by a drive mechanism.

With the support of a drive mechanism, the handling of a dental component is particularly easy. The use of a drive mechanism only requires a user to apply minimum force for initiating and/or releasing the connection between the placement device and the dental component. In addition, this may easily be achieved using only one hand.

In yet another embodiment, the insertion of the movable pin into the first engagement section biases the drive mechanism for retracting the movable pin.

A drive mechanism configured for such a biasing action can have a simple design and at the same time provides the aforementioned advantageous option of one hand control. More specifically, the drive mechanism of this embodiment is biased when coupling the dental component to the placement device. In case a treatment comprises the introduction of a dental component, the patient does not have to be present for biasing the drive mechanism. Instead, the biasing step may be performed at a factory or a dental laboratory. Once biased, the drive mechanism provides the release of the dental component from the placement device by being activated under application of minimal force, for example by pressing, lifting or turning an operating button or handle.

In a preferred embodiment of the method, the drive mechanism is activated by an actuation means, preferably for retracting the movable pin from the first engagement section.

This embodiment connects the drive mechanism with an actuation means. The actuation means may also be used for biasing the drive mechanism for placement or retraction of the dental component. Particularly for retrieving a dental component, using the actuation means for re-biasing the coupling mechanism of the placement device is advantageous since it may need several trials before retrieval of a dental component is successfully achieved.

In a preferred embodiment of the method, the dental component is placed at an implantation site. The dental component is preferably an implant, in particular a zygomatic implant.

SHORT DESCRIPTION OF THE FIGURES

The present invention will be described in the following in more detail in reference to the accompanying figures, in which.

For ease of reference, identical or similar features or features fulfilling the same function or purpose are denoted with the same or similar reference signs. Generally, same features of different embodiments are denoted using the same basic two digit reference number as the last 2 digits. For example, different embodiments of the placement device are denoted using the reference numbers 1 and 101. Unless noted otherwise, the features of these different embodiments deliver the same function and effect so that the description thereof is omitted.

DESCRIPTION OF PREFERRED EMBODIMENTS

Figure 1:
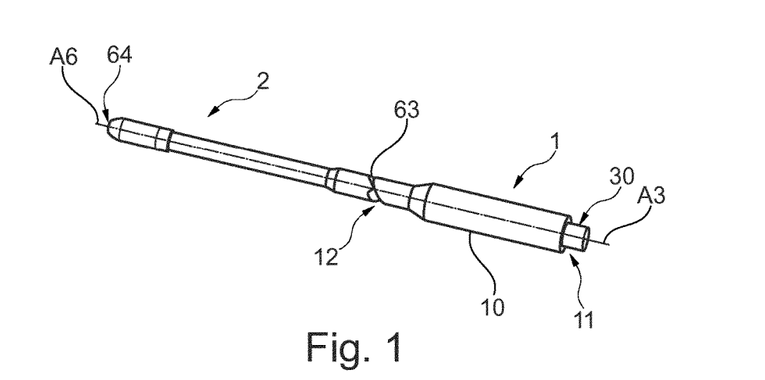
FIG. 1 shows a placement device according to the present invention in engagement with a dental component.

FIG. 1 shows a first embodiment of a placement device 1, particularly a dental placement device, which is connected to a dental component 2. The dental component 2 has a distal or apical end 64 and a proximal or coronal end 63. The dental component 2 in FIG. 1 is a dental implant, in particular a zygomatic implant. The dental component 2 may also be any other dental component such as one of the dental components listed above. The proximal end 63 of the dental component 2 is connected to the distal end 12 of the placement device 1. In other words, the dental component 2 comprises at its proximal end 63 an engagement interface 66 configured to be connected to an engagement interface 26 at the distal end 12 of the placement device 1.

As can be seen in FIG. 1, the outer dimension of the placement device 1 at its distal end 12 does not extend beyond the outer dimension of the dental component's proximal end 63.

Further, the placement device 1 has a handle 10 for handling the placement device 1. The handle 10 may be formed as a shaft and provides the user with a firm grip of the placement device 1 in order to precisely manipulate the placement device 1 and, thus, the dental component 2. It will be appreciated by the skilled person that any other form for said handle 10 may be employed in order to provide sufficient grip and control of the placement device 1. For example, the handle 10 may have an oval shape or even a spherical shape.

The proximal end 11 of the placement device 1 comprises an actuation means 30. The actuation means 30 in FIG. 1 is configured as a control knob. Said knob is preferably pressed to release the dental component 2 out of the engagement with the placement device 1.

Naturally, the actuation means 30 may also be situated at any other position on the placement device 1 that allows easy handling and operating to engage and/or release the dental component 2. Preferably the actuation means 30 is pressed or pushed in order to engage and/or disengage the dental component 2. Nonetheless, if it is more advantageous for a user handling the placement device 1, the actuation means may be operated by pushing, pulling and/or turning to operate the coupling mechanism 20.

The placement device 1 has a longitudinal axis A3, which, in the embodiment of FIG. 1, is basically aligned with the longitudinal axis A6 of the dental component 2 in order to connect the placement device 1 with the dental component 2. Thus, the longitudinal axis A3 of FIG. 1 also represents the general engagement direction of the placement device 1.

Figure 2:
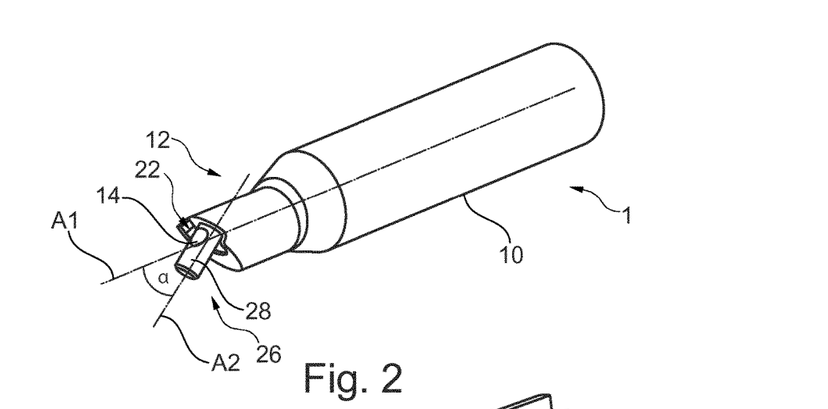
FIG. 2 shows a detailed and enlarged view of the connection interface at the distal end of the placement device.

FIG. 2 shows the distal end 12 of a first embodiment of the placement device 1 and gives a detailed view of the engagement interface 26 for establishing an engagement with a dental component 2. The engagement interface 26 comprises an engagement part 28, which is in this embodiment formed as a fixed pin, and a guide hole 14 for the movable pin 21 (cf. FIG. 3).

The coupling mechanism of the placement device 1, which enables the engagement with the dental component 2, includes the movable pin 21, the guide hole 14, and the engagement part 28.

In FIG. 2, said guide hole 14 exits the outer surface of the fixed pin 28. Accordingly, the engagement interface 66 of the dental component 2 has a corresponding first engagement section 61 and a second engagement section 62, which open up towards the engagement interface 26 of the placement device 1 for receiving the fixed pin 28 and the movable pin 21, respectively. Since the guide hole 14 is an integral part of the fixed pin 28, the first engagement section or first guide hole 61 for the movable pin 21 does not have to be sealed separately since this is automatically achieved by sealing off the second engagement section or second guide hole 62.

The second guide hole 62 may be designed to have an additional purpose besides receiving the engagement part 28. For example, after placing the dental component 2 in the mouth of a patient, the second guide hole 62 may serve for attaching another dental component using fastening means 65 (cf. FIGS. 4 and 5).

The longitudinal axis A1 of the guide hole 14 for the movable pin 21 is placed at an angle α in relation to the longitudinal axis A2 of the fixed pin 28. Said angle between the longitudinal axis A1 and the longitudinal axis A2 at the interface 26 ensures a secure anchoring within the engagement interface 66 of the dental component 2 after insertion of the fixed pin 28 into the corresponding second engagement section 62 and the subsequent insertion of the movable pin 21 into the corresponding first engagement section 61. In other words, the different orientations of the movable pin 21 and the engagement part 28 at their respective engagement interfaces 26, 66 establish a form fit or positive locking fit between the placement device 1 and the dental component 2.

The engagement interface 26 may have additional geometrical features 22 such as the annular recess shown in FIG. 2. Such an additional geometrical feature 22 may also be adapted for engagement with a dental component 2. For example, the annular recess 22 illustrated in FIG. 2 may also be configured to engage the hexagonal feature 67 of the dental component 2 (cf. FIGS. 5 and 6). Said geometrical feature may also replace the second guide hole 62 so that the engagement part 28 is basically formed as a recess and the corresponding engagement section 62 of the dental component 2 is designed as a protrusion.

Figure 3:
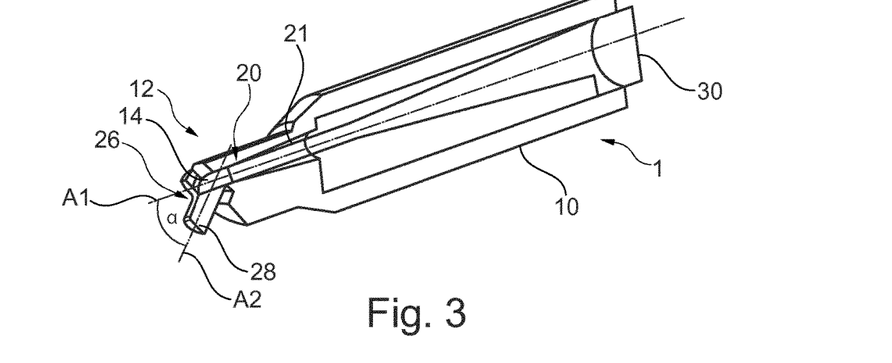
FIG. 3 shows a cross section of the distal end of the placement device shown in FIG. 2.

FIG. 3 shows a cross-sectional view of FIG. 2 for illustrating the inner configuration of the placement device 1 at its distal end 12. Particularly, the movable pin 21 is visible in its initial, retracted position within the guide hole 14 of the placement device 1. Attached to the movable pin 21 is the actuation means 30. The actuation means 30 may be complemented by an aforedescribed drive means for assisting or causing the movement of the movable pin 21. In other words, the actuation means 30 and the drive means can form an integrated unit and part of the placement device's coupling mechanism 20.

As described above, the actuation means 30 may simply be a button or handle that can be operated by a user in order to initiate the deployment or retraction of the movable pin 21. The actuation means 30 may additionally comprise a transmission in order to manipulate the force/or torque applied by a user and/or a drive means for causing the desired movement of the movable pin 21.

Thus, the activation means 30 ensures the movement of the movable pin 21 between the initial, retracted position within the placement device 1 and the extended, engagement position, which effectively interlocks the dental component 2 and the placement device 1. It will be appreciated by the skilled person that the movement of pin 21 may be a translational and/or rotational movement.

In case, the placement device 1 comprises a drive means, the force and/or torque it provides may assist the user in moving said pin 21 so that only minimum force is required by the user. This has the advantage that a user can better concentrate on positioning the placement device 1 at a predetermined position, for example during placement and release of the dental component 2 within the oral cavity of a patient or establishing a connection with a dental component 2 for retraction. The minimum action required by the user may simply be the action needed to initiate the movement of the movable pin 21 such as operating a switch for activating the coupling mechanism 20.

Further, the actuation means 30 and the drive means may be combined to form a mechanism that can be biased by operating the actuation means 30. The movement of the movable pin 21 in one direction stores the energy needed to cause the movement in the opposite direction upon subsequent activation of the actuation means 30. Such a coupling mechanism 20 is similar to the mechanisms found in ball pens, in which the drive means is generally constituted by a spring and the actuation means by a button at one end of the pen. The button operates a transmission in order to move the pen refill between a retracted position and a writing position, which in turn biases the spring. As soon as the button is pressed again, the pen refill is automatically retracted into the pen.

Figure 4:
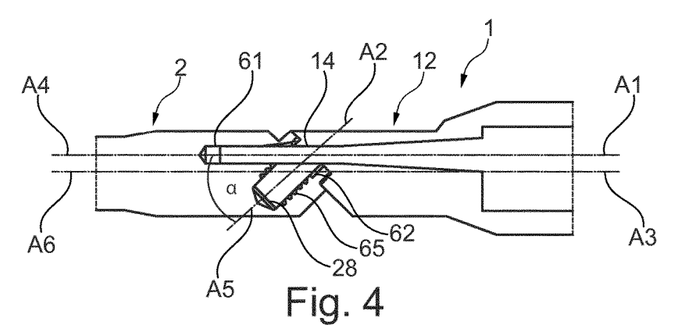
FIG. 4 shows the cross section of a placement device in engagement with the coronal end of a dental component according to a first embodiment.

FIG. 4 depicts a cross-sectional view of a placement device 1 in engagement with a dental component 2. In FIG. 4, the connection between the placement device 1 and the dental component 2 is not yet fully established. More specifically, FIG. 4 only illustrates the engagement part 28 as being introduced into the second engagement section 62 of the dental component 2. Nonetheless, it is clearly visible how the longitudinal axis A1 of the guide hole 14 for the movable pin 21 is aligned with the longitudinal axis A4 of the first engagement section 61, which is formed as a guide hole having dimensions that allow for insertion of the movable pin 21. In this position, the insertion of the movable pin 21 from the guide hole 14 of the placement device 1 into the first guide hole 61 of the dental component 2 will then establish the form fit between the device and the component.

Once inserted, the dental component 2 is locked in engagement with the placement device 1 so that a user is in a position to transmit force in all 6 degrees of freedom.

Although in the embodiments shown in the figures accompanying this description, the longitudinal axis A2 of the engagement part 28 is tilted in relation to the longitudinal axis A3 of the placement device and the axis A1 of the movable pin 21 or the guide hole 14 is located parallel to the longitudinal axis A3, the orientation of these two features of the placement device 1 and the corresponding engagement sections of the dental component 2 can easily be switched.

If the orientation of the guide hole 14 and the engagement part 28 is switched, the minimal movement still necessary in the embodiment of FIG. 4 in a direction perpendicular to the axis A6 of the dental component 2 can effectively be eliminated. This has the advantage that the distal end 12 of the placement device 1 is neither bigger than the dental component 2 in a width direction nor is the movement in said direction necessary during engagement of interface 26 and interface 66. Further, in such an embodiment, it may be advantageous to use the aforementioned flexible pin 21.

Naturally, it is also possible to put both the engagement part 28 as well as the guide hole 14 for the movable pin 21 at an angle in relation to the longitudinal axis A3 of the dental placement device 1.

Preferably, the engagement interface 26 of the placement device 1 faces in the distal direction of the dental placement device 1 so that any recesses and/or protrusions for the engagement with a dental component 2 do not increase the width perpendicular to the longitudinal axis A3 of the placement device 1.

Figure 5:
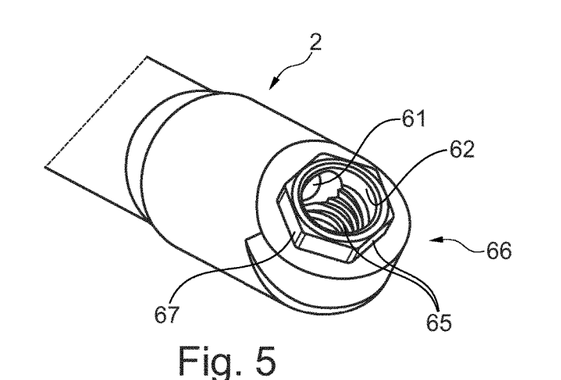
FIG. 5 shows an enlarged detailed view of a dental component's coronal interface for connection with a placement device according to a first embodiment.
Figure 6:
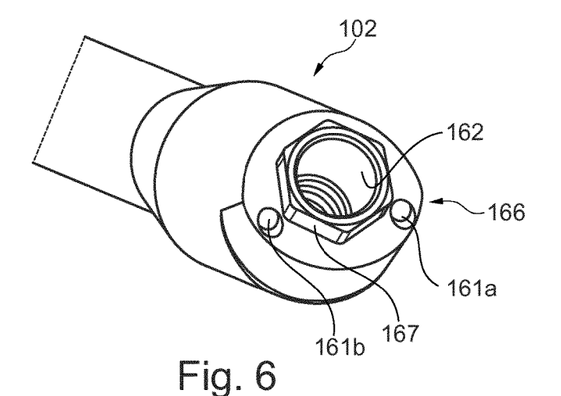
FIG. 6 shows an enlarged detailed view of a dental component's coronal interface for connection with a placement device according to a second embodiment.

The difference between the engagement interfaces of the dental components 2 and 102 shown in FIGS. 5 and 6, respectively, is simply the number and placement of the first engagement sections 61, 161a, 161b at the engagement interface 66, 166 of the dental components 2, 102.

As described above, there is only one first engagement section 61 present in FIG. 5 that is placed within the second engagement section 62, which is particularly advantageous in terms of reducing the risk of contamination before and after treatment of the patient. However, the first guide hole 61 may also be placed on the engagement interface 66 outside the first guide hole 61.

Figure 7:
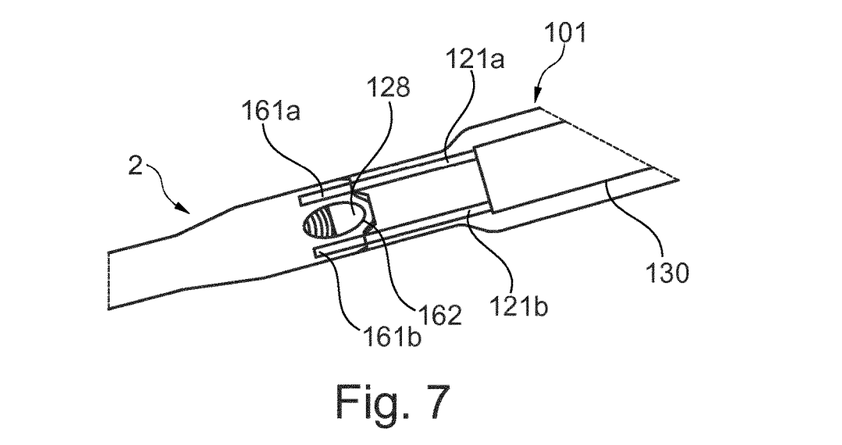
FIG. 7 shows the cross section of a placement device in engagement with the coronal end of a dental component according to a second embodiment.

The dental component 102 comprises two first engagement sections 161a, 161b in the form of guide holes. In contrast to the dental component 2 of FIG. 5, the guide holes are placed on the engagement interface 166 on both sides of the second engagement section 162 (cf. FIG. 7). This placement of the first guide holes 161a, 161b has been chosen to provide additional strength to the connection between the placement device 101 and the dental component 102.

As shown for the placement device in FIGS. 2 to 7, the engagement part is preferably designed with a higher strength than the movable pin. For example, the placement devices 1 and 101, shown in FIGS. 4 and 7, respectively, include engagement parts 28, 128 with a significantly bigger cross-section than the movable pin. This provides additional strength for transferring force and/or torque to a dental component.

This configuration also provides an advantage during the first step of engaging the dental placement device with a dental component, since it is easier for a user to guide the engagement part into the first engagement section.

The engagement part 28, 128 also provides due to its bigger size a better pre-positioning of the engagement interfaces relative to each other for aligning the guide hole(s) for the movable pin(s) with the corresponding engagement section(s). As a consequence, extending and retracting the movable pin 21, 121 is made easier.

Also in terms of strength of the engagement between the dental component and the placement device according to this invention, a small angle α between the longitudinal axis A2 of the engagement part 28 and the longitudinal axis A1 of the movable pin 21 has the advantage that the stress applied to said pin is minimized. More specifically, a smaller angle α causes less shear stress in a movable pin during interlock.

The engagement or disengagement of a placement device according to the invention and a dental component is performed as described above and may further be complemented by a locking mechanism. Such a locking mechanism ensures the movable pin to stay in its initial, retracted position, until proper engagement of the engagement part with the dental component is achieved. This prevents to incur damage to the placement device or the dental component when extending or deploying the movable pin into the corresponding engagement section of the dental component.

Further, after release of a dental component, the locking mechanism may also secure the movable pin after it has been returned to its initial, retracted position so that any unintended redeployment of the movable pin is prevented. Such a redeployment may otherwise also cause damage to the placement device, the dental component or the oral cavity of a patient.

Figure 8:
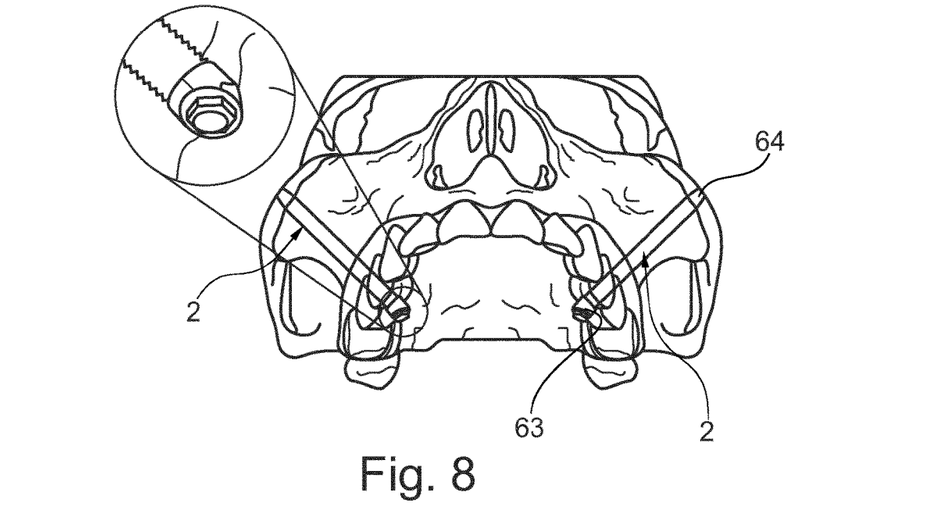
FIG. 8 shows the placement of a dental component, in particular a zygomatic implant, within the oral cavity of a patient.

FIG. 8 finally shows a preferred dental component 202 that may be used together with a placement device 1, 101 according to the invention. The dental component 202 is a zygomatic implant that can be used for anchoring a prosthetic tooth or prosthetic teeth within the oral cavity of a patient. However, this is merely an example for a dental component. Other dental components, such as the ones listed above, may also be used together with said placement device.

A more detailed description of the implantation of a zygomatic implant that may act as dental component in the present invention is provided in WO 2010/003433 A1 and is herewith incorporated by reference.

REFERENCE SIGNS 1, 101 placement device
2, 102, 202 dental component
10 handle of implant placement device
11 proximal end of placement device
12 distal end of placement device
14 guide hole
20 coupling mechanism
21, 121a, 121b movable pin
22 geometrical features of engagement interface
26 engagement interface of placement device
28, 128 engagement part
30, 130 actuation means
61, 161a, 161b first engagement section/first guide hole
62, 162 second engagement section/second guide hole
63 proximal or coronal end of dental component
64 distal or apical end of dental component
65 fastening means
66, 166 engagement interface of dental component
67 geometrical feature of the dental component
A1 longitudinal axis of movable pin/guide hole
A2 longitudinal axis of engagement part
A3 longitudinal axis of placement device
A4 longitudinal axis of first engagement section
A5 longitudinal axis of second engagement section
A6 longitudinal axis of dental component
α angle between A1 and A2

The invention claimed is:

1. A placement device for a dental component, the placement device comprising a proximal end, a distal end and a coupling mechanism for coupling the distal end to the dental component in order to allow the application of force and torque, wherein the coupling mechanism includes:
  at least one movable pin having a longitudinal axis and being movable along its longitudinal axis relative to the placement device for engaging a proximal end of the dental component;
  at least one engagement part at the distal end of the placement device for engaging the proximal end of the dental component, the engagement part having a longitudinal axis, wherein the longitudinal axis of the engagement part is arranged at an angle relative to the longitudinal axis of the movable pin.

2. The placement device according to claim 1, wherein the engagement part is aligned along a longitudinal axis of the placement device.

3. The placement device according to claim 1, wherein the coupling mechanism further comprises an actuation member for moving said movable pin between a retracted position and an engaged position.

4. The placement device according to claim 3, wherein the actuation member is adapted to apply a rotation to the movable pin.

5. The placement device according to claim 3, wherein the actuation member further comprises a drive mechanism for at least assisting in an extension and/or retraction of said movable pin.

6. The placement device according to claim 1, wherein the angle between the longitudinal axis of said movable pin and the longitudinal axis of said engagement part is between 3° to 80°.

7. The placement device according to claim 1, further comprising a locking mechanism arranged to lock the position of the movable pin in at least one of its retracted position and engaged position.

8. A dental component for coupling to a placement device according to claim 1, the dental component comprising a proximal end and a distal end, the proximal end constituting an interface for the placement device, wherein the interface comprises:
at least one first engagement section having a first longitudinal axis defined therethrough, the first engagement section being for interacting with a movable pin of the placement device, and
at least one second engagement section having a second longitudinal axis defined therethrough, the second engagement section for interacting with an engagement part of the placement device,
wherein the first longitudinal axis is arranged at an angle relative to the second longitudinal axis.

9. The dental component according to claim 8, wherein the first engagement section is arranged within the second engagement section.

10. An implantation set comprising a placement device according to claim 1 and a dental component comprising a proximal end and a distal end, the proximal end constituting an interface for the placement device, wherein the interface comprises:
at least one first engagement section having a first longitudinal axis defined therethrough, the first engagement section being for interacting with a movable pin of the placement device, and
at least one second engagement section having a second longitudinal axis defined therethrough, the second engagement section for interacting with an engagement part of the placement device,
wherein the first longitudinal axis is arranged at an angle relative to the second longitudinal axis.

11. A method for handling a dental component with a placement device, according to claim 1, comprising the steps:
moving the placement device along or about a first axis for engaging at least one engagement part situated at a distal end of the placement device with a second engagement section of the dental component,
inserting at least one movable pin of the placement device into a first engagement section of the dental component along or about a second axis,
wherein an orientation of a longitudinal axis of the engagement part differs from the orientation of a longitudinal axis of the movable pin.

12. The method according to claim 11, wherein the engagement of the engagement part releases a locking mechanism of the placement device for enabling a movement of the movable pin.

13. The method according to claim 11, wherein at least one of the insertion and the retraction of the movable pin is at least assisted by a drive mechanism.

14. The method according to claim 13, wherein the insertion of the movable pin into the first engagement section biases the drive mechanism for retracting the movable pin.

15. The method according to claim 13, wherein the drive mechanism is activated by an actuation member.

* * * * *